(12) United States Patent
Probst

(10) Patent No.: US 11,505,756 B2
(45) Date of Patent: Nov. 22, 2022

(54) FOOD-GRADE ETHANOL

(71) Applicant: Laurent Probst, Alfortville (FR)

(72) Inventor: Laurent Probst, Alfortville (FR)

(73) Assignee: Laurent Probst, Alfortville (FR)

( * ) Notice: Subject to any disclaimer, the term of this patent is extended or adjusted under 35 U.S.C. 154(b) by 840 days.

(21) Appl. No.: 16/342,555

(22) PCT Filed: Oct. 23, 2017

(86) PCT No.: PCT/FR2017/052914
§ 371 (c)(1),
(2) Date: Apr. 17, 2019

(87) PCT Pub. No.: WO2018/078267
PCT Pub. Date: May 3, 2018

(65) Prior Publication Data
US 2020/0054047 A1     Feb. 20, 2020

(30) Foreign Application Priority Data

Oct. 27, 2016   (FR) ........................................ 1670637

(51) Int. Cl.
*C10L 7/04* (2006.01)
*A23L 13/00* (2016.01)
(Continued)

(52) U.S. Cl.
CPC ................ *C10L 7/04* (2013.01); *A23C 13/12* (2013.01); *A23G 9/48* (2013.01); *A23L 5/19* (2016.08);
(Continued)

(58) Field of Classification Search
CPC .. A23L 15/30; A23L 5/19; A23L 13/03; A23P 20/15; C10L 7/04; A61Q 13/00;
(Continued)

(56) References Cited

U.S. PATENT DOCUMENTS

| 3,795,747 A | 3/1974 | Mitchell et al. |
| 3,964,880 A | 6/1976 | Siegrist |

(Continued)

FOREIGN PATENT DOCUMENTS

| FR | 2178983 A1 | 11/1973 |
| JP | S551035 A | 1/1980 |

(Continued)

OTHER PUBLICATIONS

International Search Report and Written Opinion in corresponding International Patent Application No. PCT/FR2017/052914 dated Feb. 6, 2018. 15 pages.

*Primary Examiner* — Vishal V Vasisth
(74) *Attorney, Agent, or Firm* — Leason Ellis LLP

(57) ABSTRACT

The present invention concerns an ethanol with an alcohol by volume between 85% and 99%, and comprising a Hydroxy-Alkyl-Cellulose, the dosage of Hydroxy-Alkyl-Cellulose being limited so as to obtain a dynamic viscosity of less than 100 Pa·s.

This invention also concerns the use of such ethanol as combustible for cooking a foodstuff, or part of a foodstuff, in particular for safely cooking in the immediate vicinity of the person for whom the food is intended, so as to use cooking as a show.

8 Claims, 1 Drawing Sheet

(51) Int. Cl.
  *A23L 5/10* (2016.01)
  *A23P 20/15* (2016.01)
  *A23L 15/00* (2016.01)
  *A23C 13/12* (2006.01)
  *A23G 9/48* (2006.01)
  *C12G 3/005* (2019.01)

(52) U.S. Cl.
  CPC .............. *A23L 13/03* (2016.08); *A23L 15/30* (2016.08); *A23P 20/15* (2016.08); *C12G 3/005* (2013.01); *A23V 2002/00* (2013.01)

(58) Field of Classification Search
  CPC ........ A61Q 17/005; A61K 8/34; A23C 13/12; C12G 3/005; A61P 31/04; A23G 9/48; A23V 2002/00; A01N 31/02
  See application file for complete search history.

(56) References Cited

U.S. PATENT DOCUMENTS

| | | | |
|---|---|---|---|
| 5,961,707 | A | 10/1999 | Mothes et al. |
| 6,755,877 | B2 * | 6/2004 | Perlman .................. C10L 11/06 44/451 |

FOREIGN PATENT DOCUMENTS

| | | |
|---|---|---|
| JP | S551035 B2 | 1/1980 |
| JP | 61195194 A | 8/1986 |
| JP | S6363777 A | 3/1988 |
| JP | 01305043 A | 12/1989 |
| JP | 02286789 A | 11/1990 |
| JP | 04088088 A | 3/1992 |
| KR | 20120135748 A | 12/2012 |
| WO | 2005002406 A1 | 1/2005 |
| WO | 2014162086 A1 | 10/2014 |

* cited by examiner

FOOD-GRADE ETHANOL

CROSS-REFERENCE TO RELATED PATENT APPLICATIONS

This application is a U.S. National Stage Application under 35 U.S.C. § 371 of International Patent Application No. PCT/FR2017/052914, filed Oct. 23, 2017, which claims the benefit of priority under 35 U.S.C. Section 119(e) of French Patent Application number FR1670637 filed Oct. 27, 2016, both of which are incorporated by reference in their entireties. The International Application was published on May 3, 2018, as International Publication No. WO 2018/078267 A1.

The present invention is in the field of cooking. It concerns in particular an improved food-grade ethanol that can be used in different food recipes, in particular as a controlled cooking means to make it a show for the guest or customer. The ethanol is then spread in a receptacle to be burnt and release the corresponding heat, or the ethanol is spread on the food, for example a cream, so that the combustion of the ethanol produces the effect of creme brulee.

It is known, by a patent application filed by the applicant, no EP1 635 683, a pure ethanol cooking process. When a pure ethanol is ignited, particularly one with alcohol by volume above 80%, it first ignites at room temperature, without the need for preheating, and then burns completely. This effect is desired for dishes such as creme brulee, where we try to make a caramelization by producing a flame on its surface, or meat or fish or tarte flambee, for which we want to add a flavour after cooking; we then take an ethanol in which we add a flavour, spread it on the surface of the dish, ignite it at room temperature, and the ethanol is burnt entirely, leaving the only flavour on the surface of the dish, with a grilled effect on the surface of the dish.

However, in order to achieve this result, ethanol must not be left with the air and on the surface of the dish for too long, otherwise it dilutes with the water in the dish, or the humidity in the ambient air. After only a few minutes, the ethanol has diluted, it becomes more difficult to ignite, and it no longer consumes completely, the water in the ethanol extinguishing the flame before all the ethanol has been burnt. However, when we want to propose such a method to a table of several people, for example, it may be interesting to put ethanol on everyone's dishes, and then set them on fire at the same time. It is therefore common that one or two minutes pass between the first ethanol deposit and its ignition.

Yet, such possibilities are highly appreciated, and correspond to a demand from users. Indeed, customers of a restaurant appreciate to see their creme brulee ignite and form in front of their eyes, or to see an egg cooking in an egg cup with a visible flame or to see a skewer cooking in front of their eyes. And they enjoy, when they are together, to see these shows perform at the same time on all the plates of the table.

The inventor realized that by adding a small amount of hydroxy-alkyl cellulose to the ethanol, it diluted much less quickly in the surrounding water, and for an ethanol that was sufficiently concentrated at first, it becomes possible to ignite the ethanol several minutes after it was put, even on a very wet dish. For ethanol with an alcohol by volume between 80 and 85%, the ethanol is not completely consumed at room temperature, and it is better to avoid this percentage range.

The purpose of this invention is to compensate at least in part for these disadvantages. For this purpose, it proposes an ethanol with an alcohol by volume between 85% and 99% including a Hydroxy-Alkyl-Cellulose (HAC), said HAC being dosed to obtain a viscosity lower than 100 Pa·s.

Thanks to these arrangements, ethanol according to the invention can easily be uniformly put on the surface of, for example, a creme brulee, or cooked meat or fish. The amount of HAC to be used in order not to exceed the claimed dynamic viscosity depends strongly on the type of HAC used, but the person skilled in the art knows perfectly how to dose HAC, by using abacuses, or by a few simple tests. Moreover, by proposing an ethanol with an alcohol by volume between 85% and 99%, we make sure that the ethanol ignites, despite the addition of a small percentage of HAC, and we avoid too expensive ethanol production processes for removing the last percentage of water.

According to other characteristics:
said HAC may be a Hydroxy-Propyl-Cellulose (HPC), this product giving particularly satisfactory results,
the dosage of Hydroxy-Propyl-Cellulose can be at least 1 g per litre of ethanol, this dosage allowing to obtain the desired effect of not diluting the alcohol with water.

The present invention also concerns the use of an ethanol according to the invention as combustible for cooking a foodstuff, or part of a foodstuff. This allows to take a bit of time between the contact of ethanol with the foodstuff and/or with the ambient air, and its ignition.

According to other characteristics:
said cooking can take place in the immediate vicinity of the person for whom said foodstuff is intended, so as to use the cooking as a show in front of a guest or a customer sitting at his table for a meal; the advantage of this method is that the ethanol can be calmly put on a dish of a guest, then on the dishes of every other guest around the table, then several servers can organize themselves to ignite the ethanol of all the dishes on the table at the same time,
said foodstuff may be an egg placed in a transparent container, said ethanol being placed in a tank outside the container, thereby allowing the egg to be observed being cooked,
said foodstuff may be a skewer, for example of meat or fish, said ethanol being placed in a half cylinder, and the skewer being placed on said half cylinder, allowing a clean and odourless cooking,
said cooking may consist in caramelizing a cream to make a creme brulee; a layer of cellulose is also obtained, in a very surprising way, on the surface of the creme brulee, and this layer is impermeable to water, and therefore protects the creme brulee from ambient humidity; the creme brulee can thus be served several hours after the caramelization, without losing the crunchiness of the crust formed, which does not prevent it from being savoured immediately,
said use may include the following steps:
ethanol is placed in a pencil-type container,
ethanol is put on a foodstuff using said pencil, following a particular drawing,
the ethanol is ignited,
it allows time between the putting of the ethanol on the foodstuff and the ignition of the ethanol,
said use may include the following steps:
pearl making
encapsulation of these pearls, for example by surrounding them with an algae
introduction of the obtained pearls into ice creams,
thus making it possible to obtain non-frozen pearls at ice cream freezing temperatures, around −18° C.

This invention will be better understood when reading the following detailed description, with reference to the attached figures in which.

The inventor has long sought a solution for users, guests or restaurant customers, by cooking before their eyes. He was familiar with the solution of ethanol with an alcohol by volume above 80%, which allows for odourless cooking and complete combustion of the ethanol. However, this ethanol makes it necessary to be very fast, otherwise it dilutes with the surrounding water and evaporates very quickly. However, in some cases, we would like to have a little more time.

The inventor has therefore carried out many tests with various products. He found that by adding a small amount of Hydroxy-Alkyl-Cellulose to an ethanol with an alcohol by volume between 85 and 99%, dilution with water is very much slower, and evaporation is also slowed down.

The inventor realized that in order to achieve a satisfactory effect, and to sufficiently reduce the dilution with water, the amount of HAC must be at least 1 g of HAC per litre of ethanol. In addition, in order to be used satisfactorily, the ethanol must preferably have a dynamic viscosity under 100 Pa·s, above which the ethanol becomes too difficult to spread. These viscosities can be obtained, for example, with a HPC with a molecular weight of 100,000 g/mol dosed at 60 g/litre of ethanol.

This result can also be obtained with a HPC with a molecular weight of 850,000 g/mol dosed at less than 20 g/litre of ethanol.

The viscosity value is measured "at rest", i.e. at a shear rate of $0.1 \ s^{-1}$. This specification is important because the dynamic viscosity decreases as the shear rate increases. In this patent application, whenever a viscosity is involved, it is understood that it is the dynamic viscosity at rest, i.e. at a shear rate of $0.1 \ s^{-1}$.

Depending on the type of HAC used, the dynamic viscosity increases more or less quickly for a given added amount, and it is important for the application to be limited to 100 Pa·s, otherwise it becomes very difficult to spread the ethanol obtained, or to make it go out from a pencil. It is even better to limit to 50 Pa·s in order to obtain a product that is pleasant to handle.

The person skilled in the art knows perfectly how to dose the HAC to obtain a given dynamic viscosity.

Various products of the Hydroxy-alkyl-Cellulose family, such as HPC, but also Hydroxy-Ethyl-Cellulose, Hydroxy-Ethyl-Methyl-Cellulose, or Hydroxy-Propyl-Methyl-Cellulose, may be used to achieve a similar effect of slowing down the water absorption of the obtained ethanol.

Figure 1:
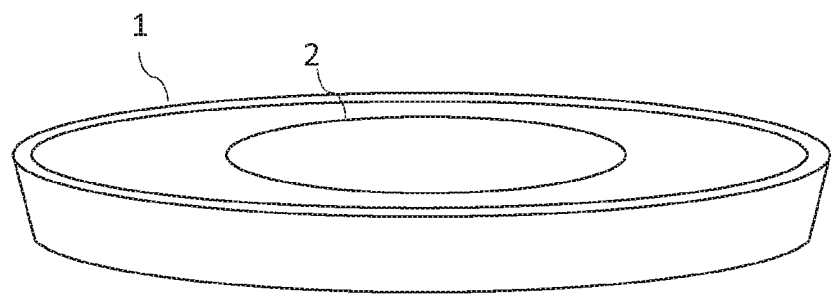
FIG. 1 shows a plate with a dish, for example meat
Figure 2:
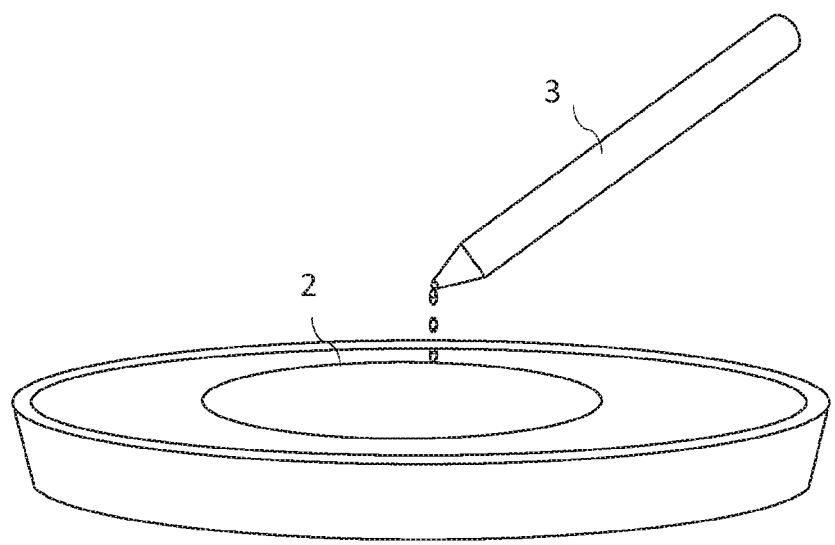
FIG. 2 shows the plate of FIG. 1, with putting an ethanol according to the invention using a pencil
Figure 3:
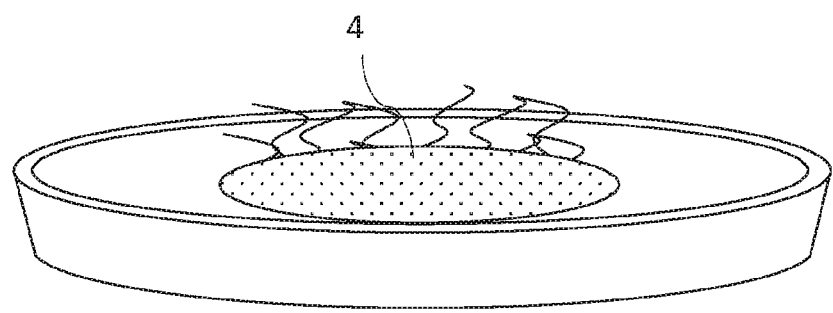
FIG. 3 shows the plate of FIG. 1, with the dish flaming.

Such ethanol can be flavoured and then used to cook and brown fish or meat. The said fish 2 can be placed in a plate 1 (see FIG. 1). Then (FIG. 2), using a pencil 3 containing an ethanol according to the invention, place said ethanol on the fish 2. It is possible to wait until everything is ready, then ignite the ethanol, and see it burn (FIG. 3). A fish with a thin golden crust 4 is obtained, resulting from the grilling of a thin layer of fish.

For example, an ethanol with an alcohol by volume of 95% can be taken, to which a quantity of 20 g/l of HPC at 850,000 g/mol is added. The ethanol can be placed calmly while the plate is placed in front of the guest. Not only does the ethanol according to the invention not dilute itself with water from the dish, or from the surrounding air, but in addition, because of the greater amount of HPC used, and the characteristic of HPC to increase the viscosity of the alcohol, it remains in place on the dish where it was put, and flows only very little. This makes it much more practical to carry out.

It is therefore possible to wait until the right time to ignite it with a lighter or a match. The ethanol then burns until it is completely consumed. It also significantly improves safety for the user, since it significantly reduces the risk of ethanol, particularly inflamed ethanol, escaping in the event of a rollover or a knocking of the plate. The latter advantage is found in virtually all the applications mentioned in the present application.

It remains then a thin layer of cellulose, completely invisible, and the aromas, as well as a thin layer of the dish roasted under the effect of the heat released by the combustion of ethanol.

The invention can be used to produce the caramelization of a cream to make a creme brulee. When a cream is caramelized with a conventional ethanol, for example rum or whisky with an alcohol volume of 40% (or 80-proof with the Anglo-Saxon measure), a flame is obtained that lasts less than 10 s. A sufficient quantity of ethanol has therefore to be put in so that the heat released in less than 10 s makes it possible to obtain a satisfactory caramelization. With a very pure ethanol, a flame is obtained that can last 30 to 40 s, and the ethanol is completely consumed. This has the advantage that there is no ethanol taste left on the creme brulee, and that the amount of ethanol required is much lower.

However, when using conventional pure ethanol, there is a risk that the ethanol spills, especially if the cream pot is pushed during combustion, which can always happen. Caramelization is therefore most often done in the kitchen, where safety conditions can be ensured, and then the creme brulee is served to the guest or customer. However, it must be served within 30 to 45 minutes at most, otherwise the humidity in the ambient air softens the crust, which is no longer crispy, which is quite a problem for a creme brulee. In addition, ethanol must be ignited immediately, as soon as it is placed on the cream, otherwise it has time to dilute with the humidity of the ambient air, or with the condensation water on the cream, or absorbed by brown sugar or caramel flakes.

With an ethanol according to the invention, for example at 1.5 g/l of HPC, the ethanol does not absorb humidity from the ambient air or condensation water; consequently, the ethanol can be placed on the cream in the kitchen and then ignited in front of the guest.

In addition, the crust remains crispy for more than three hours. The combustion leaves a very thin layer of cellulose, invisible, but impermeable to the humidity of the ambient air, and thus protects the creme brulee, which makes it possible to prepare the cremes brulees in advance, or to make them burn in front of the guest, according to the needs of the moment.

Ethanol according to the invention can also be used in an egg cup, the egg being placed in a transparent container, and ethanol according to the invention in a tank placed under the container, for example an egg cup such as those described in the french patents FR3004095 and FR3029094. Ethanol according to the invention not being diluted by water from the surrounding air, it can be placed in the tank in the kitchen, then brought to the table, and only then ignited, for example at the same time for several guests.

For similar reasons, it can be used advantageously in a skewer device, such as the one described in the european patent EP1635683.

Another use of ethanol according to the invention is in the field of edible pearls. According to the state of the art, strong ethanol, such as rum or cointreau, can be encapsulated after it has been gelled. Such an ethanol with a high alcohol by volume of about 50% and its encapsulation is done by surrounding it with an algae, highly loaded with water. The result is a pearl with an alcohol by volume around 20%, or even 17%. Sometimes it is desired to integrate such pearls into an ice cream to produce a pleasant effect under the tongue. However, at the storage temperature of ice cream, in a freezer at −18° C., an ethanol with an alcohol volume of 20% or 17% freezes, and becomes solid.

By taking an ethanol according to the invention, for example with 10 or 15 g of HPC per litre of ethanol, and adding a rum or cointreau flavouring, it can be encapsulated and it is possible to obtain pearls with an alcohol by volume of 40%. In such percentages, ethanol remains liquid at −18° C., and the desired effect in ice cream at this temperature is perfectly achieved.

Another use of ethanol according to the invention is in the field of hand sanitizer gels. For this purpose, ethanol can be placed in a pencil. When a user wishes to disinfect his hands, he can take out the ethanol according to the invention and spread it on his hands. By rubbing his hands, he produces the evaporation of ethanol and disinfects his hands. Of course, it can be combined with a chosen perfume, which remains on the hands after the ethanol has evaporated.

Yet another use of ethanol according to the invention is a use to flavour a dish. Instead of sprinkling or spraying the dish with a perfume, the perfume is introduced into the ethanol according to the invention, placed on the dish, and ignited. When the ethanol has burned out, the perfume is impregnated on the surface of the dish, and there is no trace of the ethanol left.

The invention claimed is:

1. A method of cooking using a composition comprising: (i) a food grade ethanol as combustible for cooking wherein the ethanol is between 85% and 99% by volume; and (ii) Hydroxy-Alkyl-Cellulose, wherein the composition has a dynamic viscosity under 100 Pa·s at rest at ambient temperature.

2. The method according to claim 1 in the immediate vicinity of a person for whom said food is intended, so as to use the cooking as a show.

3. The method according to claim 1 for cooking an egg in a container, said ethanol being placed in a tank outside the container.

4. The method according to claim 1 for cooking a skewer, said ethanol being placed in a half cylinder, and the skewer being placed on said half cylinder.

5. The method according to claim 1 to caramelize a cream, and make it into a creme brulee.

6. The method according to claim 1, wherein said Hydroxy-Alkyl-Cellulose is an Hydroxy-Propyl-Methyl-Cellulose.

7. The method according to claim 6, wherein the Hydroxy-Propyl-Methyl-Cellulose is at least 1 g per liter of ethanol.

8. The method of according to claim 4, wherein the skewer is a meat skewer or a fish skewer.

* * * * *